(12) United States Patent
Korman et al.

(10) Patent No.: US 12,201,324 B2
(45) Date of Patent: Jan. 21, 2025

(54) BONE FIXATION IMPLANT AND METHOD OF IMPLANTATION

(71) Applicant: WRIGHT MEDICAL TECHNOLOGY, INC., Memphis, TN (US)

(72) Inventors: Zachary Korman, Memphis, TN (US); David Redfern, Hove (GB)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 374 days.

(21) Appl. No.: 17/653,899

(22) Filed: Mar. 8, 2022

(65) Prior Publication Data

US 2022/0313328 A1 Oct. 6, 2022

Related U.S. Application Data

(60) Provisional application No. 63/167,901, filed on Mar. 30, 2021.

(51) Int. Cl.
*A61B 17/56* (2006.01)
*A61B 17/68* (2006.01)
*A61B 17/86* (2006.01)

(52) U.S. Cl.
CPC ......... *A61B 17/56* (2013.01); *A61B 17/864* (2013.01); *A61B 17/8685* (2013.01); *A61B 2017/681* (2013.01); *A61B 17/8635* (2013.01)

(58) Field of Classification Search
CPC ... A61B 17/56; A61B 2017/681; A61B 17/86; A61B 17/8605; A61B 17/8615; A61B 17/862; A61B 17/864; A61B 17/8685; A61B 17/8875; A61B 17/888; A61B 17/8891
See application file for complete search history.

(56) References Cited

U.S. PATENT DOCUMENTS

| 4,878,794 | A | 11/1989 | Potucek |
| 6,224,598 | B1 | 5/2001 | Jackson |
| 7,204,838 | B2 | 4/2007 | Jackson |
| 8,343,200 | B2* | 1/2013 | Khanna ............ A61B 17/8685 606/304 |
| 9,095,444 | B2* | 8/2015 | Melkent ............ A61B 17/7059 |
| 9,585,703 | B2* | 3/2017 | Munday ............ A61B 17/7225 |
| 2012/0245701 | A1* | 9/2012 | Zak ............ A61F 2/4202 623/21.18 |

(Continued)

FOREIGN PATENT DOCUMENTS

DE 202007017159 U1 5/2008
WO 2018021987 A1 2/2018

OTHER PUBLICATIONS

Extended European Search Report issued in connection with corresponding Patent Application No. 22161390.4, Nov. 2, 2022, 11 pages.

(Continued)

*Primary Examiner* — Larry E Waggle, Jr.
(74) *Attorney, Agent, or Firm* — Duane Morris LLP

(57) ABSTRACT

Provided is a nested screw assembly and a related method for fusing a joint between two bones using the nested screw assembly, where the nested screw assembly includes a cannulated outer screw and an inner screw.

6 Claims, 9 Drawing Sheets

(56) References Cited

U.S. PATENT DOCUMENTS

2013/0215381 A1     8/2013  Raghuprasad
2014/0107712 A1*    4/2014  Fallin .................... A61F 2/4225
                                                            606/328

OTHER PUBLICATIONS

Partial European Search Report issued in connection with corresponding Patent Application No. 22161390.4, Aug. 1, 2022, 12 pages.

* cited by examiner

BONE FIXATION IMPLANT AND METHOD OF IMPLANTATION

CROSS-REFERENCE TO RELATED APPLICATIONS

This application claims priority under 35 U.S.C. § 119(e) to U.S. Provisional Application No. 63/167,901, filed Mar. 30, 2021, the entirety of which is incorporated herein by reference.

FIELD

This disclosure relates generally to a screw-based construct for forming a bone-to-bone fixation.

BACKGROUND

Currently, with screw-based constructs for forming bone-to-bone fixation of a joint, surgeons must compromise between obtaining compression and obtaining significant stability. When forming bone-to-bone fixation, compression screws provide optimal compression but not optimal stability. On the other hand, with proper technique, full-threaded constant-pitch screws can provide more stability but not optimal compression. There is a need for a screw construct and a technique for using the screw construct that can accomplish both.

SUMMARY

Provided is a method for fusing a joint between a first bone and a second bone using a nested screw assembly that comprises: a cannulated outer screw; and an inner screw, wherein: the outer screw comprises: a tubular body having a first end and a second end defining a length between the two ends; and a canal extending through the length of the outer screw. At least a portion of the length of the outer screw is externally threaded and at least a portion of the length of the canal is internally threaded near the first end. The inner screw is externally threaded, and the external thread of the outer screw, the internal thread of the outer screw, and the external thread of the inner screw all have the same thread pitch, whereby the inner screw can be threaded into the first end of the canal of the outer screw to form the nested screw assembly. The method comprises: (a) pre-drilling a hole into the first bone and the second bone through the joint; (b) threading the outer screw into the hole in the first bone up to the joint; (c) threading the inner screw into the hole in the second bone from the opposite side until the inner screw engages with the internally threaded portion of the outer screw from the first end of the outer screw, and tightening to compress the joint while holding the outer screw from turning; and (d) driving the outer screw further into the hole toward and across the joint to maintain compression of the joint.

Also provided is a nested screw assembly comprising: a cannulated outer screw; and an inner screw, wherein, the outer screw comprises a tubular structure having a first end and a second end defining a length between the two ends, and a canal extending through the length of the outer screw, at least a portion of the length of the outer screw is externally threaded and at least a portion of the length of the canal is internally threaded near the first end, the inner screw is externally threaded, and the external thread of the outer screw, the internal thread of the outer screw, and the external thread of the inner screw all have the same thread pitch, whereby the inner screw can be threaded into the first end of the canal of the outer screw to form the nested screw assembly.

BRIEF DESCRIPTION OF THE DRAWINGS

These and other features and advantages of the bone fixation implants and methods of implantation described herein will be more fully disclosed in, or rendered obvious by, the following detailed description of the preferred embodiments, which is to be considered together with the accompanying drawings wherein like numbers refer to like parts and further wherein.

Figure 1A:
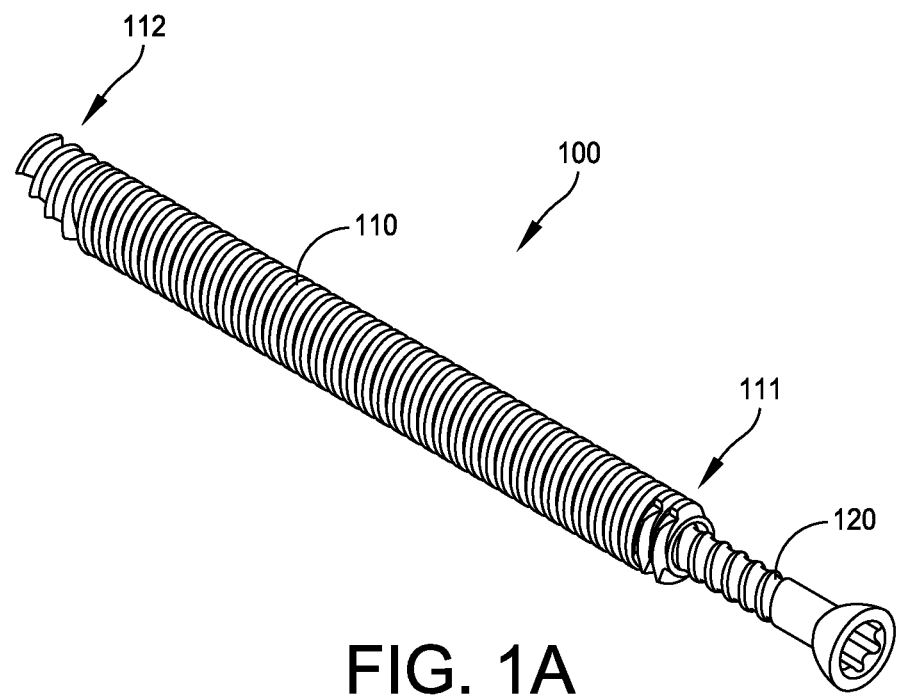
FIG. 1A is an illustration showing an isometric view of an embodiment of a nested screw assembly according to the present disclosure.
Figure 1B:
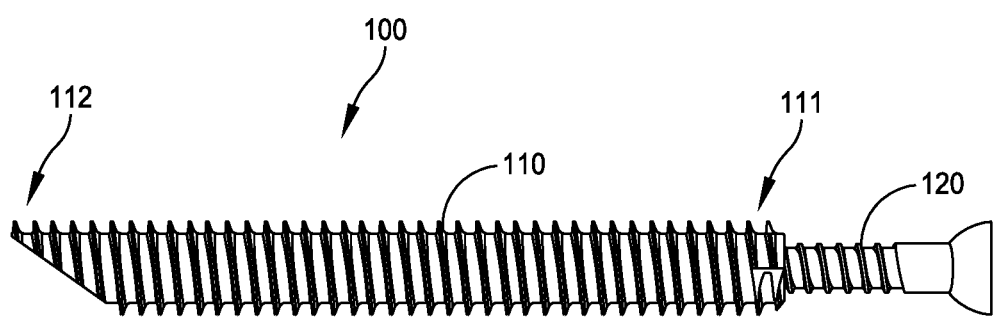
FIG. 1B is an illustration showing a plan view of the nested screw assembly of FIG. 1A.

All illustrations shown in the figures are schematic and are not intended to show actual dimensions or proportions.

DETAILED DESCRIPTION

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Disclosed is a novel method for fusing a joint between two bones using a nested screw assembly. An example of an application of the disclosed novel method is fusing the first tarsometatarsal (TMT) joint in a Lapidus procedure.

Referring to FIGS. 1A-6, a nested screw assembly 100 according to an embodiment is disclosed. The nested screw assembly 100 comprises a cannulated outer screw 110 and an inner screw 120 that is threaded into the cannulated outer screw 110.

Figure 3:
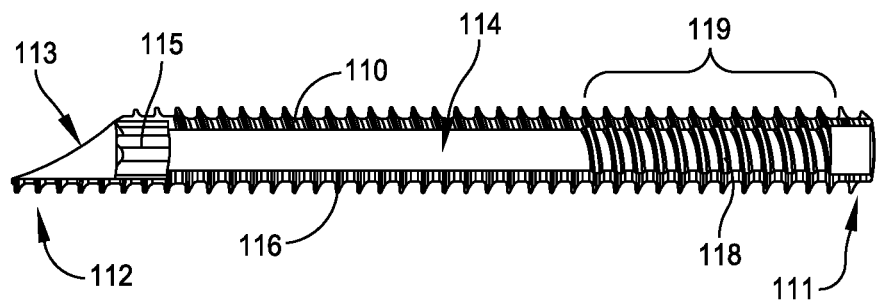
FIG. 3 is a longitudinal cross-sectional view of the outer screw component.

Referring to FIG. 3, in some embodiments, the outer screw 110 comprises a body that is a tubular structure having a first end 111 and a second end 112 defining a length between the two ends, and a canal 114 extending through the length of the outer screw 110. At least a portion of the length of the outer screw is externally threaded with threading 116 and at least a portion 119 of the length of the canal 114 is internally threaded with threading 118 near the first end 111. In the illustrated example in FIG. 3, the whole length of the exterior surface of the outer screw 110 is threaded.

Figure 2A:
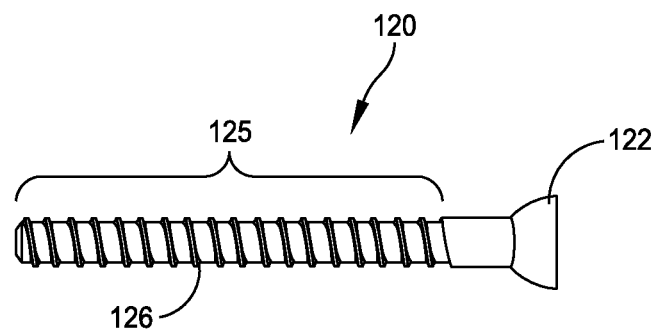
FIG. 2A is an illustration of an inner screw component of the nested screw assembly shown in FIG. 1A where the inner screw is a headed screw.
Figure 2B:
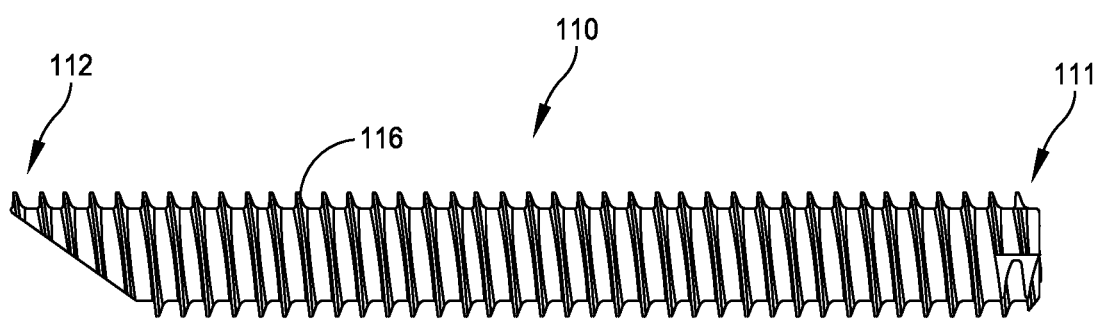
FIG. 2B is an illustration of an outer screw component of the nested screw assembly shown in FIG. 1A.

Referring to FIG. 2A, the inner screw 120 comprises a body, a substantial portion 125 of which is externally threaded with threading 126. The internal thread 118 of the outer screw and the external thread 126 of the inner screw have the same thread pitch so that the inner screw 120 can be threaded into the first end 111 of the canal 114 of the outer screw 110 to form the nested screw assembly 100. The external thread 116 of the outer screw 110 is also configured to have the same thread pitch and handedness as the internal thread 118 of the outer screw and the external thread 126 of the inner screw.

Figure 4:
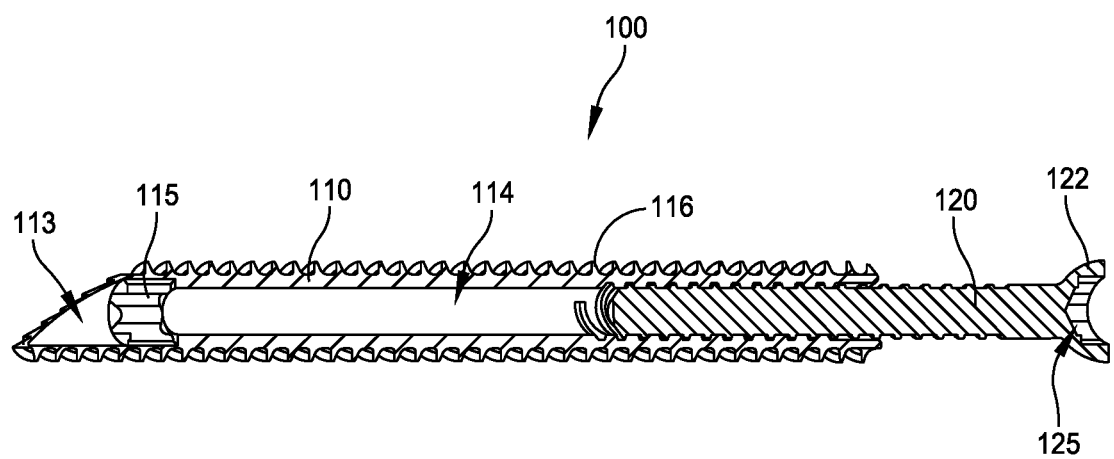
FIG. 4 is a longitudinal cross-sectional view of the nested screw assembly shown in FIGS. 1A-1B.

Referring to FIGS. 2A and 4, in some embodiments of the nested screw assembly, the inner screw 120 comprises an oval head 122. The head 122 can be provided with a socket 125 for receiving a driver tool bit for screwing/unscrewing the inner screw 120.

Figure 5:
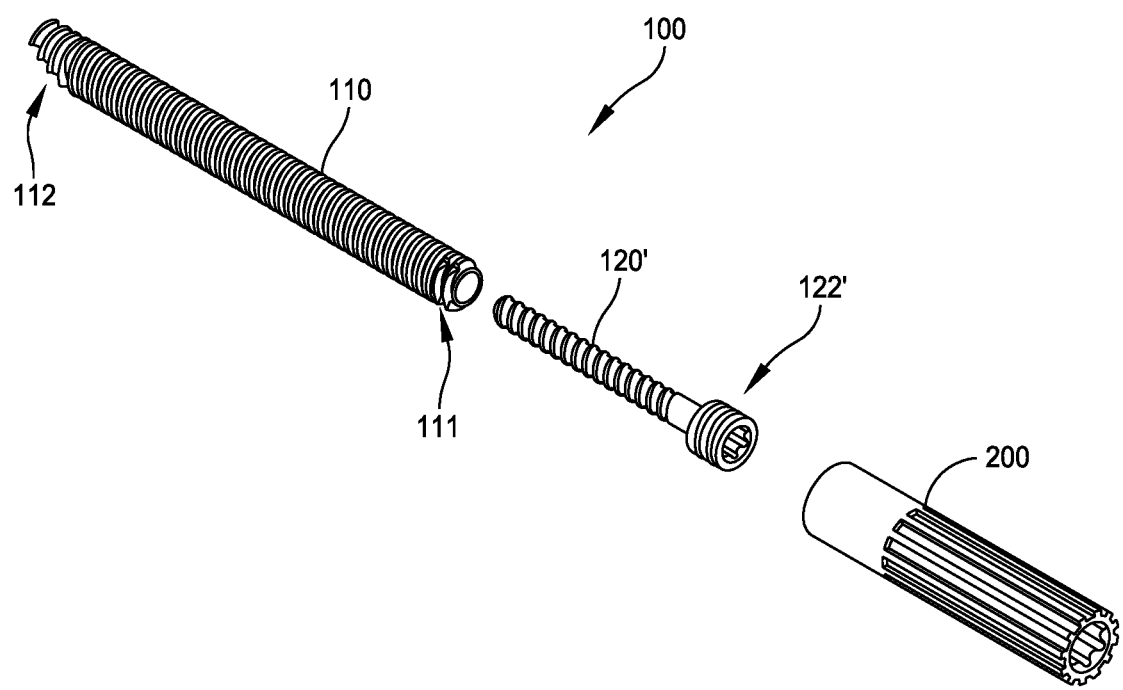
FIG. 5 is an exploded view of a nested screw assembly according to another embodiment where the inner screw is a headless screw.
Figure 6:
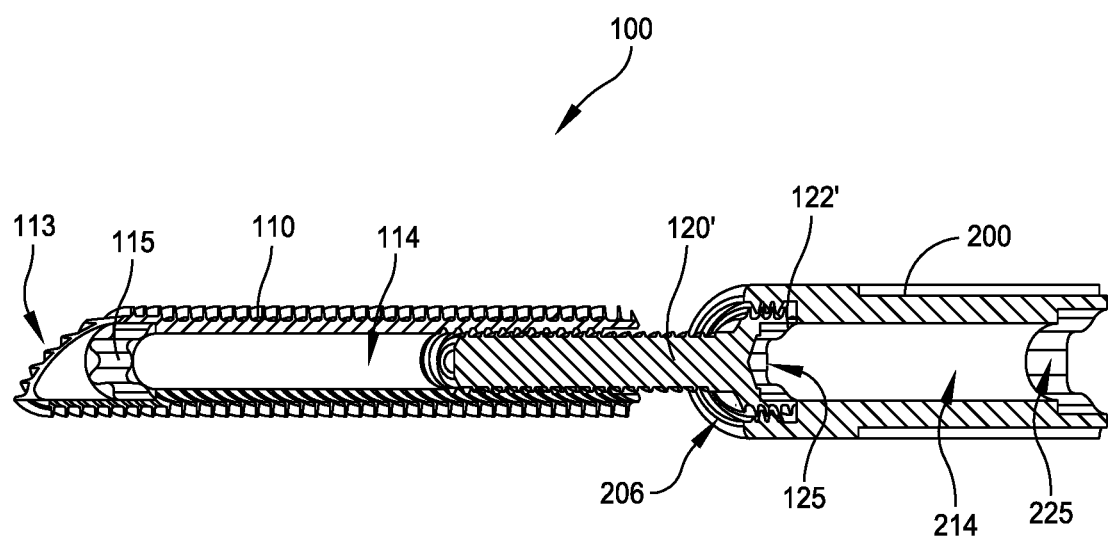
FIG. 6 is a longitudinal cross-sectional view of an embodiment of the nested screw assembly shown in working engagement with a compression sleeve.

Referring to FIGS. 5 and 6, in another embodiment, the inner screw 120' is a headless type and comprises a threaded head portion 122' with a thread pitch that is different from the thread pitch of the external thread 116 of the outer screw, the internal thread 118 of the outer screw, and the external thread 126 of the inner screw 120'. In some embodiments, the thread pitch on the threaded head portion 122' is smaller than the thread pitch of the other threads.

In some embodiments, the outer screw 110 further comprises a driving feature 115 provided inside the canal 114 near the second end 112. The driving feature 115 can be a socket, such as a hex socket, star drive socket, etc. The driving feature 115 enables the outer screw 110 to be screwed into a bone using an appropriate drive bit inserted into the second end opening 113 (see FIGS. 3-4).

In the embodiment of the nested screw assembly 100 where the inner screw 120' has the threaded head portion 122', a compression sleeve 200 can be used to drive the inner screw 120' into the outer screw 110. The longitudinal cross-sectional view in FIG. 6 shows the nested screw assembly 100 and the compression sleeve 200 engaging the threaded head portion 122' of the inner screw 120'. The compression sleeve 200 comprises an internally threaded opening 206 at one end for engaging the threaded head portion 122' of the inner screw 120'. The compression sleeve 200 can also be provided with a tool receiving socket 225 on the opposite end for receiving a driver tool for turning the compression sleeve 200.

Figure 7:
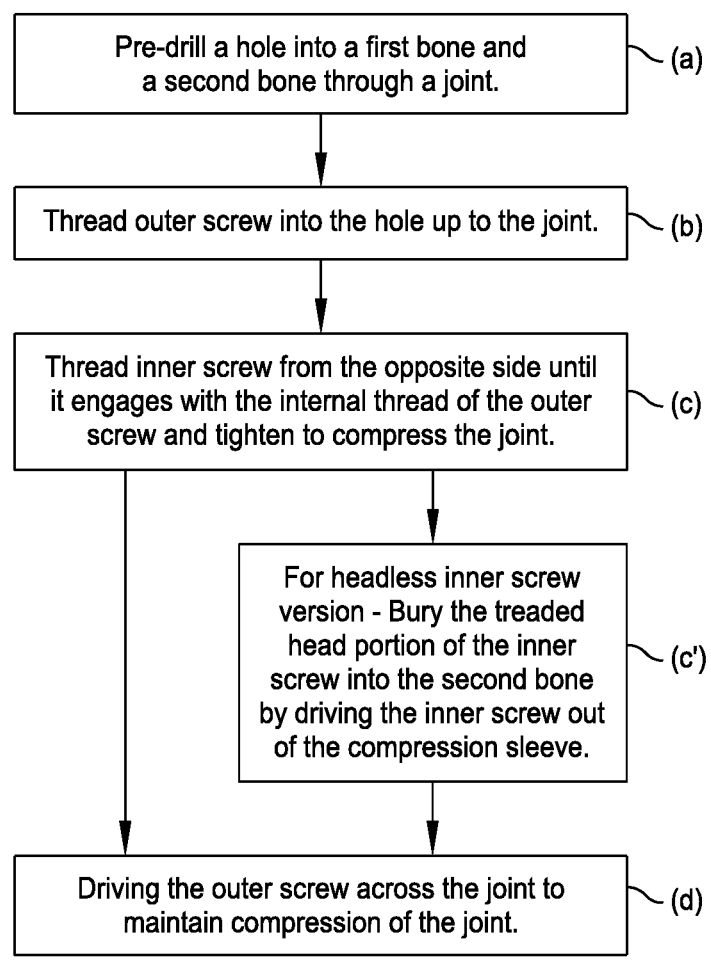
FIG. 7 is a flowchart illustrating an example of a procedure for using the nested screw assembly of the present disclosure in fusing a joint.
Figure 8A:
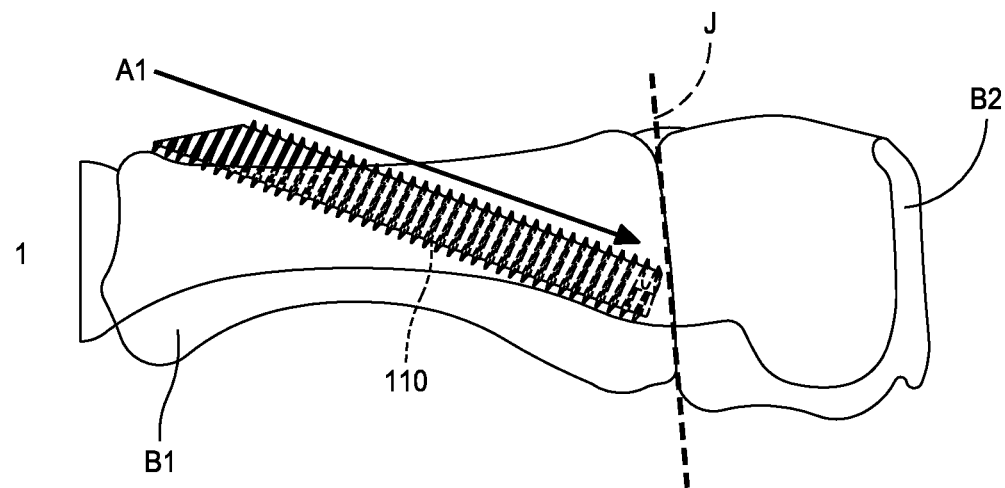
FIGS. 8A-8D are illustrations showing two bones B1 and B2 of a joint J being compressed using the nested screw assembly according to the present disclosure.
Figure 8B:
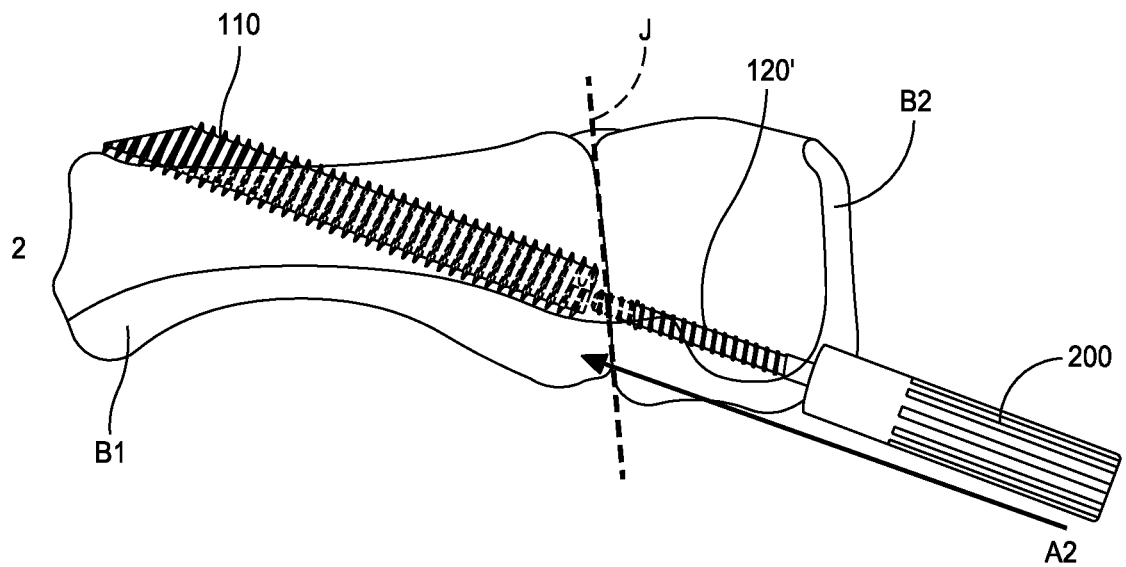

Referring to the flowchart 10 in FIG. 7 and the FIGS. 8A-8D, a method for fusing a joint between two bones using the nested screw 100 will be described. A method for fusing a joint between a first bone B1 and a second bone B2 using the nested screw assembly 100 comprises the following procedures. First, (a) a hole is pre-drilled into the first bone B1 and the second bone B2 through the joint. The joint is indicated by the line J in FIG. 8A. Then, referring to FIG. 8A, (b) the outer screw 110 is screwed/threaded into the hole in the first bone B1 up to the joint J. The direction of the outer screw's advancement into the first bone B1 is indicated by the arrow A1. Referring to FIG. 8B, next, (c) the inner screw 120' is screwed/threaded into the hole in the second bone B2 from the opposite side until the inner screw 120' engages with the internally threaded portion 119 of the outer screw 110 from the first end 111 of the outer screw and form a nested screw assembly. The direction of the inner screw's advancement here is indicated by the arrow A2 in FIG. 8B. Then, to compress the two bones B1, B2 together at the joint, the inner screw 120' is tightened while holding the outer screw 110 from turning. The outer screw 110 can be held in place from turning using a driver tool that is inserted into the second end 112 of the outer screw to engage the driving feature 115 in the canal 114. The inner screw 120 can be driven using the compression sleeve 200. As illustrated in FIG. 8B, with the compression sleeve 200 engaged to the threaded head portion 122' of the inner screw 120', because the compression sleeve 200 has a larger diameter than the inner screw 120 and the hole in the second bone B2, as the inner screw 120' is threaded into the outer screw 110 and advanced in the direction of the arrow A2 with respect to the first bone B1 and the outer screw 110, the compression sleeve 200 comes in contact with the second bone B2 and compresses the second bone B2 toward and against the first bone B1. Once the desired compression of the two bones B1, B2 is achieved, the compression sleeve 200 is removed. See FIG. 8C.

If an embodiment of the nested screw assembly 100 that comprises the oval headed inner screw 120 (see FIG. 2A) is used, as the inner screw 120 is threaded into the outer screw 110 and advance in the direction of the arrow A2 with respect to the first bone B1 and the outer screw 110, the head 122 of the inner screw 120, rather than the compression sleeve 200, will come into contact with the second bone B2 and compress the second bone B2 toward and against the first bone B1. Thus, when the oval headed inner screw 120 is used, the compression sleeve 200 is not needed as a standard screwdriver can be used with the oval headed inner screw 120.

Figure 8C:
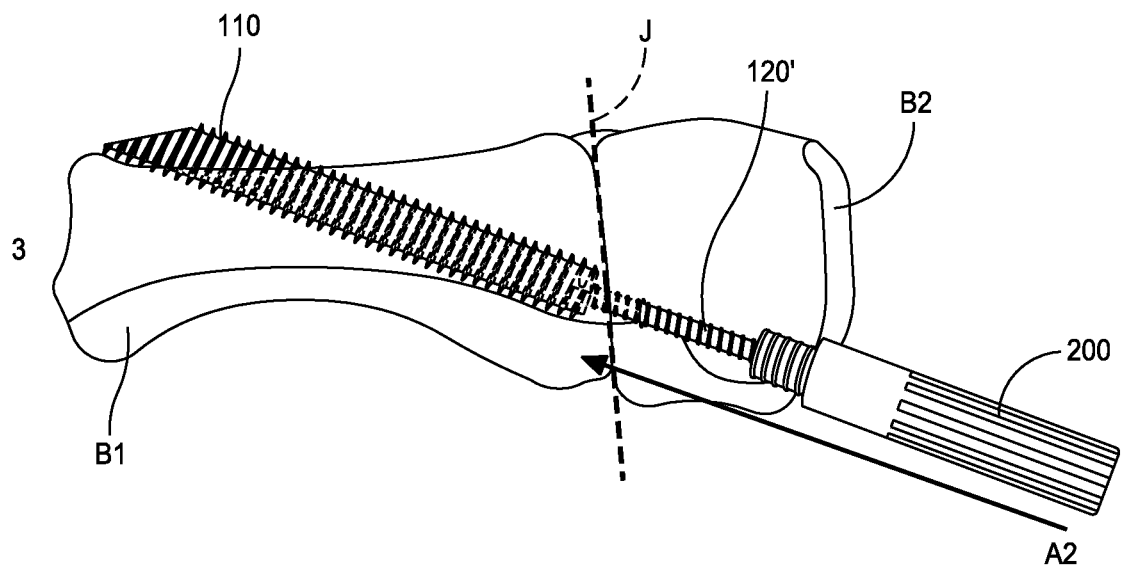
Figure 8D:
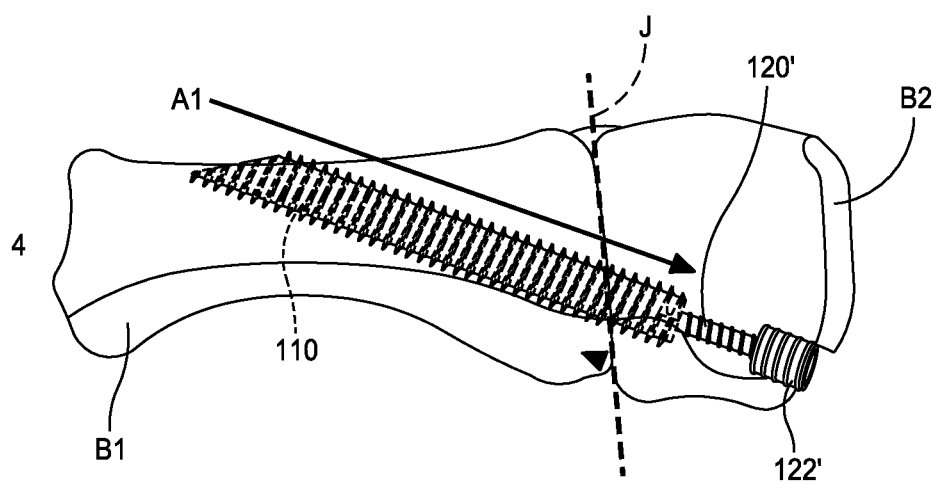

Referring to FIG. 8D, after the compression of the two bones B1, B2 is achieved, (d) the outer screw 110 is screwed further into the hole in the first bone B1 in the direction A1, toward and across the joint J to maintain the compression of the joint. This procedure is carried out while the inner screw 120 is held in place using a driver bit inserted into the tool socket 125 of the inner screw. This procedure is possible because the external thread 116 of the outer screw 110 has the same thread pitch and handedness as the internal thread 118 of the outer screw and the external thread 126 of the inner screw. With the inner screw 120 in place, the outer screw can be driven across the joint because the outer screw threads across the bone at the same rate it threads over the inner screw 120.

For the embodiment where the headless inner screw 120' with the threaded head portion 122' is used, after the step (c), the threaded head portion 122' of the inner screw 120' is buried into the second bone B2, so that the head portion 122' is not protruding from the bone B2, by driving the inner screw 120' out of the compression sleeve 200. This is illustrated in FIG. 8C. This step of burying the head portion 122' of the inner screw 120' into the second bone B2 can be done either before or after the outer screw 110 is advanced across the joint J. FIG. 8D shows the position of the headless inner screw 120' after the head portion 122' is buried into the second bone B2.

Figure 9:
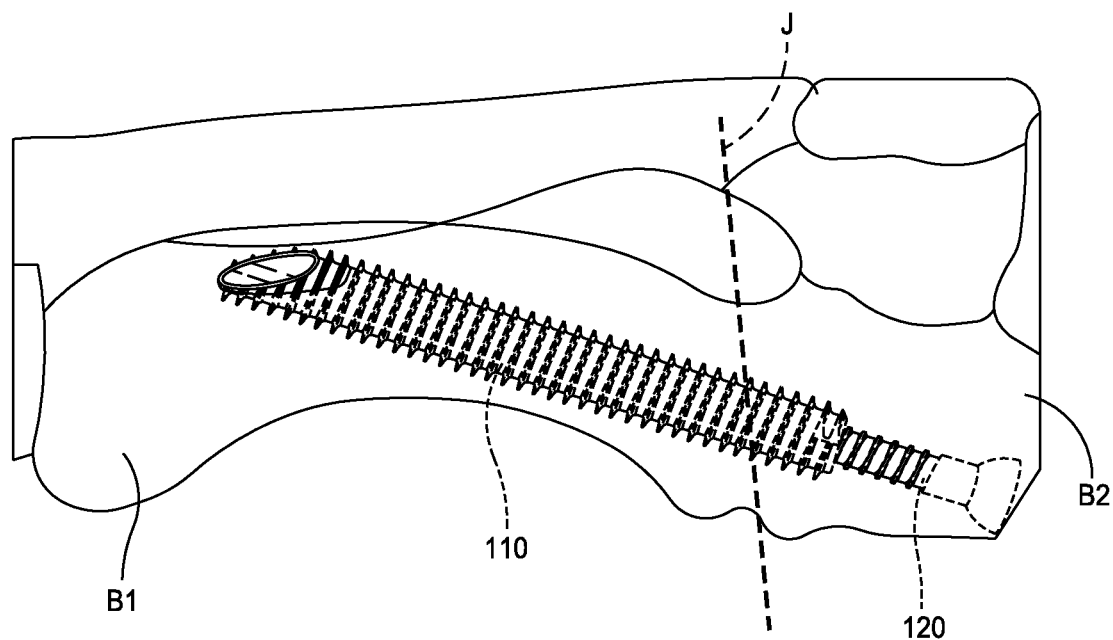
FIG. 9 is an illustration showing the nested screw assembly embodiment, where an oval headed inner screw is used, after the compression of the bones B1, B2 is completed.

FIG. 9 is an illustration showing the nested screw assembly embodiment where the oval headed inner screw 120 is used rather than the headless inner screw 120' after the compression of the bones B1, B2 is completed.

Referring to FIG. 6, in some embodiments, the outer screw 110 comprises a driving feature 115 provided inside the canal 114 near the second end 112, and the outer screw is threaded into the hole in the procedure (b) by engaging the driving feature 115 with a driving tool.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the claimed devices, kits, systems, and methods.

What is claimed is:

1. A method for fusing a joint between a first bone and a second bone using a nested screw assembly that comprises:
   a cannulated outer screw; and
   an inner screw,
   wherein, the outer screw comprises a tubular body having a first end and a second end defining a length between the two ends, and a canal extending through the length of the outer screw, at least a portion of the length of the outer screw is externally threaded and at least a portion of a length of the canal is internally threaded near the first end, the inner screw is externally threaded, and the external thread of the outer screw, the internal thread of the outer screw, and the external thread of the inner screw all have the same thread pitch, whereby the inner screw can be threaded into the first end of the canal of the outer screw to form the nested screw assembly, the method comprising:
   (a) pre-drilling a hole into the first bone and the second bone through the joint;
   (b) threading the outer screw into the hole in the first bone up to the joint;
   (c) threading the inner screw into the hole in the second bone from an opposite side until the inner screw engages with the internal thread of the outer screw from the first end of the outer screw, and tightening to compress the joint while holding the outer screw from turning; and
   (d) driving the outer screw further into the hole toward and across the joint to maintain compression of the joint.

2. The method of claim 1, wherein the outer screw comprises a driving feature provided inside the canal near the second end, and the outer screw is threaded into the hole in step (b) by engaging the driving feature with a driving tool.

3. The method of claim 2, wherein the outer screw is held in step (c) using the driving feature.

4. The method of claim 1, wherein the inner screw comprises an oval head portion and threading the inner screw in step (c) is accomplished using a screwdriver that engages the oval head portion.

5. The method of claim 1, wherein the inner screw comprises a threaded head portion and threading the inner screw in step (c) is accomplished using a compression sleeve that engages the threaded head portion.

6. The method of claim 5, wherein after step (c) but before step (d), the threaded head portion of the inner screw is buried into the second bone by driving the inner screw out of the compression sleeve.

* * * * *